United States Patent [19]

Arvizu Barragan

[11] 3,943,926

[45] Mar. 16, 1976

[54] WHOLLY DISPOSABLE DENTAL TYPE SYRINGE

[76] Inventor: Oscar Arvizu Barragan, Insurgentes Sur 1768, ler. Piso, Mexico City, Mexico

[22] Filed: Aug. 29, 1974

[21] Appl. No.: 501,576

[30] Foreign Application Priority Data

Apr. 10, 1974 Mexico .................................. 150546

[52] U.S. Cl. ......................... 128/218 DA; 128/218 P
[51] Int. Cl.² ............................................ A61M 5/00
[58] Field of Search ..... 128/218 P, 218 D, 218 DA, 128/218 M, 218 C, 218 R, 218 N, 220, 215, DIG. 5, 221; 206/363–367, 438

[56] References Cited

UNITED STATES PATENTS

| | | | |
|---|---|---|---|
| 1,771,219 | 7/1930 | Hein | 128/218 P |
| 2,555,878 | 6/1951 | Drabicki | 128/218 D |
| 2,720,880 | 10/1955 | Whitaker et al. | 128/218 D |
| 3,259,130 | 7/1966 | Krauthamer | 128/218 R |
| 3,366,103 | 1/1968 | Keller | 128/DIG 5 |
| 3,712,301 | 1/1973 | Sarnoff | 128/218 D |
| 3,820,652 | 6/1974 | Thackston | 128/221 X |

FOREIGN PATENTS OR APPLICATIONS 1,181,037   2/1970   United Kingdom ............. 128/218 R

*Primary Examiner*—John D. Yasko
*Attorney, Agent, or Firm*—Ladas, Parry, Von Gehr, Goldsmith & Deschamps

[57] ABSTRACT

The present invention refers to an improved, wholly disposable dental type syringe, comprising: a hollow, transparent cylindrical body which includes one open end having integral ears, and the other end closed, in which latter end is mounted a needle for injecting having two points, and on the inside of the hollow cylindrical body, ribs extending throughout its entire length; a piston which is hollow and open at one end, and includes in its closed end suction means, and at its open end curved arms, the piston being also the protector for the needle; and adjusting and guiding means, which holds an ordinary dental anesthesic cartridge in contact with the closed end of the hollow cylindrical body and, at the same time, guides the travel of the piston, the adjusting and guiding means being the protector for the suction means while the piston is the protector of the needle.

2 Claims, 8 Drawing Figures

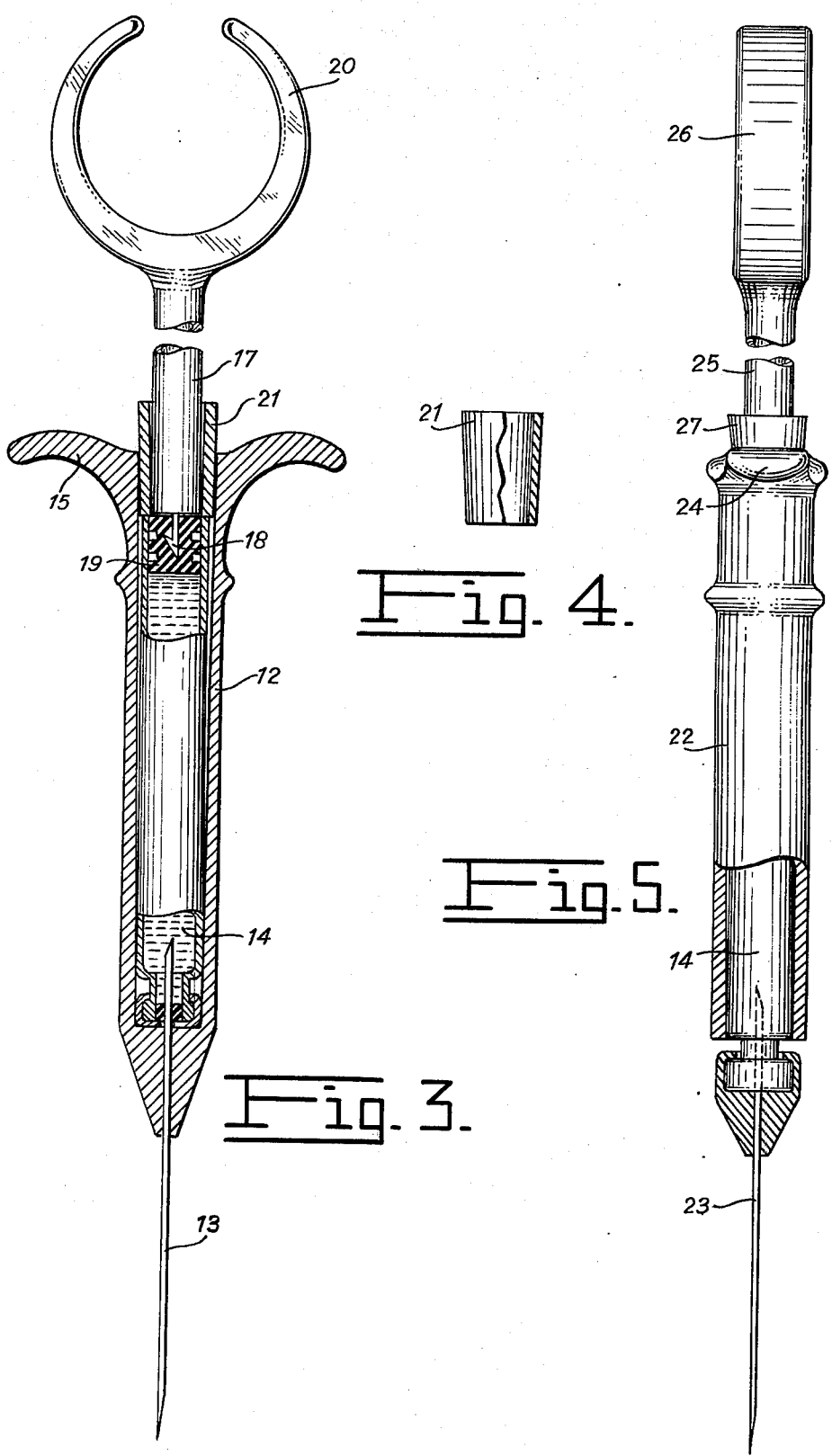

WHOLLY DISPOSABLE DENTAL TYPE SYRINGE

BACKGROUND OF THE INVENTION

In the field of odontology we find that devices for applying anesthetics for local blockage consist only of a body in the form of a hollow cylinder and a piston, both metallic, to which devices for applying anesthetics an injection needle must be attached in order to use them.

These known devices for applying anesthetics present substantial drawbacks. Thus, as above indicated, they require separate needles, representing an additional expense.

Another problem presented by the known devices for applying anesthetics is the fact that, since the hollow cylindrical body is metallic, it must necessarily incorporate a window to permit observing the quantity of anesthetic applied to the patient. The window involves an added step of manufacture in forming the body of the device for applying anesthetics.

Another drawback presented by the known devices for applying anesthetics is the fact that there is no way to determine if a blood vessel has been struck, since there is no means for applying suction.

In addition to the problems mentioned, the known devices for applying anesthetics present the drawback that each time they are needed for use, it is necessary to sterilize them.

Finally, in addition to the drawbacks mentioned and the extra expense which they occasion, the known device is itself quite expensive, and we may conclude, uneconomic.

OBJECTS OF THE INVENTION

It is accordingly one object of the present invention to provide an improved, wholly disposable dental type syringe, which is not merely a body and a piston but includes suction means, adjusting and guiding means, and an injection needle integrally mounted.

A further object of the present invention is to provide an improved, wholly disposable dental type syringe, which does not involve additional expense for the purchase of separate needles.

It is another object of the present invention to provide an improved, wholly disposable dental type syringe which does not require a window in order to observe the quantity of anesthetic administered to the patient because the body thereof is itself transparent. Furthermore, by the same token, in the manufacture of the syringes covered by the present invention no additional step is required to produce such window.

It is an additional object of the present invention to provide an improved wholly disposable dental type syringe with which it can be definitely determined if a blood vessel has or has not been struck, since it includes such suction means.

Another object of the present invention is to provide an improved wholly disposable dental type syringe which is obtained in sterile condition at the time of its purchase and which, accordingly, does not require sterilizing when anesthetic is to be applied to a patient.

Still another object of the present invention is to provide an improved wholly disposable dental type syringe which is very economical and practical.

Consequently, the present invention provides an improved wholly disposable dental type syringe comprising: a transparent, hollow, cylindrical body which includes one open end on which there are integral ears, and the other end closed, in which closed end is fixed a needle for injecting having two points, and on the interior of the said hollow cylindrical body there are ribs along its entire length; a hollow piston open at one of its ends, which includes on its closed end suction means, and at its open end curved arms, said piston also being the protector for the needle; and adjusting and guiding means which holds an ordinary dental anesthetic cartridge so that it remains in contact with the closed end of the hollow cylindrical body, and also guides the travel of the piston, said adjusting and guiding means being also the protector of the suction means when the said piston is the protector of the needle.

These and other objects to be obtained through the use of the present invention will be more clearly understood and better appreciated by means of the following description, which refers to the drawings of the preferred embodiment of the present invention.

DESCRIPTION OF THE DRAWINGS

FIG. 3 is a conventional detailed cross-sectional view illustrating the wholly disposable dental type syringe of the present invention with a cartridge of dental anesthetic included within it.

FIG. 4 is a conventional broken longitudinal cross-sectional view of the adjusting and guiding means of the dental type syringe of the present invention.

FIG. 5 is a detailed view in conventional cross-section which illustrates another embodiment of the dental type syringe of the present invention.

DETAILED DESCRIPTION OF THE INVENTION

Figures 1, 2:
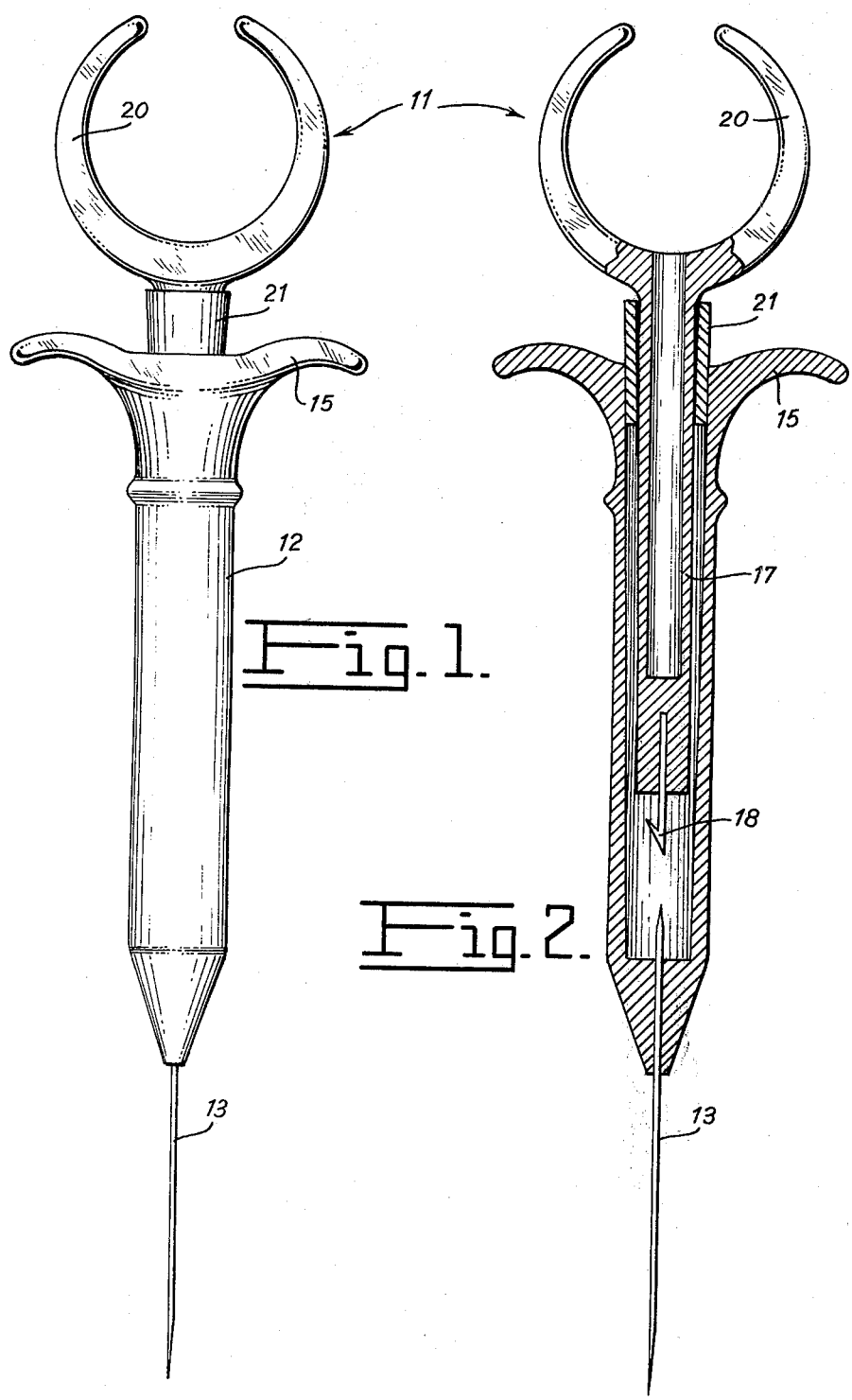
FIG. 1 is a vertical elevational view, which illustrates the wholly disposable dental type syringe of the present invention.
FIG. 2 is a longitudinal cross-sectional view of the wholly disposable dental type syringe of the present invention.
Figure 6:
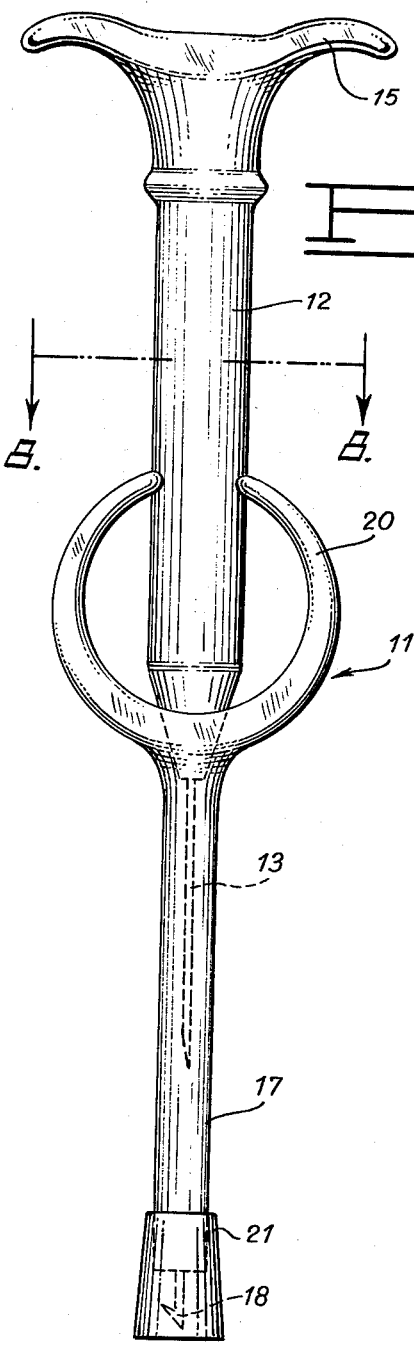
FIG. 6 is a vertical elevational view of the wholly disposable dental type syringe of the present invention, which shows the piston protecting the needle and the adjusting and guiding means protecting the suction means.
Figure 7:
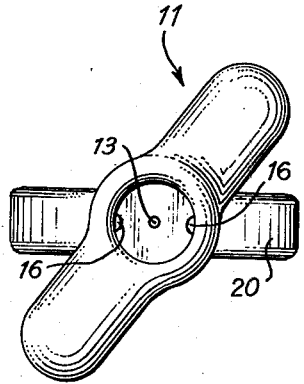
FIG. 7 is a top plan view of the wholly disposable dental type syringe when the piston is protecting the needle.
Figure 8:
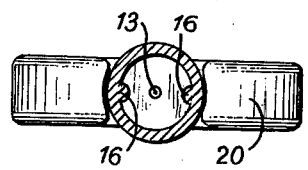
FIG. 8 is a view in cross-section along line 8 — 8 of FIG. 6, which shows how the piston is secured to the hollow cylindrical body when said piston is protecting said needle.

The present invention refers to devices for applying anesthetic for local blockage, and specifically to improvements in a wholly disposable dental type syringe 11 which is composed of a transparent hollow cylindrical body 12 which latter has one closed end in which is integrally secured an injection needle having two points 13. That point of the needle 13 which is held in the closed end of the transparent body 12 must project in such manner as to perforate an ordinary cartridge of dental anesthetic 14 (see FIG. 3).

On the open end of the hollow transparent cylindrical body 12 there are included integral ears 15 curving slightly toward the hollow transparent cylindrical body 12, which provide support for the dentist's fingers when using the wholly disposable syringe 11 of the present invention.

On the inside of the hollow cylindrical body 12 ribs 16 are provided along its entire length, said ribs 16 being not of uniform thickness, but rather somewhat thicker in their portion registering with the end portion of the cylindrical body 12 which carries the injection needle 13, said thickness diminishing to a minimum at portion registering with the open end of said cylindrical body 12. By means of these ribs 16 the cartridge of anesthetic 14 is compelled to remain under pressure in the interior of the syringe 11, thus becoming substantially fixed thereto, hence assuring the discardable character of the device of this invention, since it cannot be reused because the anesthetic cartridge 14 cannot be removed.

The wholly disposable syringe 11 includes, in addition, a hollow piston 17 which is open at one end and which includes at its closed end a suction device 18.

The suction device 18 is a metallic component the end of which has the form of a harpoon head for corkpuller in order to effect positive engagement when it pierces a rubber plug 19 carried by all known types of dental anesthetic cartridges 14 at the end of said cartridges 14 which is opposite to that in which the needle 13 penetrates, in order to produce suction when the hollow piston 17 drawn outward after the patient has been injected, for the purpose of determining if a blood vessel has been struck.

The hollow piston 17 carries on its open end curved arms 20 the ends of which are directed toward one another to form a slightly open ring, the opening in which is sufficiently small so that the thumb of the person using the dental syringe does not pass through, and yet sufficiently large so that said opening will engage upon the hollow transparent cylindrical body 12. The ends of the arms 20 are also slightly concave in order to engage the cylindrical body 12 adequately, as above indicated. The said disposition is required, since the hollow piston 17 shields the needle 13 when the disposable syringe 11 is packaged for sale.

In addition to the foregoing components, the dental syringe 11 includes an adjusting and guiding device 21 which forces the dental anesthetic cartridge 14 to register with the end of the cylindrical body 12 which includes the injection needle 13, in order that said needle 13 may penetrate into the inside of the dental anesthetic cartridge 14 above referred to, so that the anesthetic solution can be applied. At the same time, the adjusting and guiding device 21 guides the travel of the hollow piston 17.

The adjusting and guiding device 21 is of annular and frustro-conical shape, with a height of axial dimension slightly greater than the distance from the open end of the cylindrical body 12 to the corresponding end of the anesthetic cartridge, When the latter has been placed completely inside the said cylindrical body 12. Thus by means of the adjusting and guiding device 21 the anesthetic cartridge is pressed against the ribs 16 until it reaches the required position within the syringe 11. Furthermore, also because of the abovementioned ribs 16, the adjusting and guiding device 21 becomes perfectly attached to the open end of the cylindrical body 12, so that its removal becomes very difficult, thus providing another of the characteristics tending to the total discard of the dental type syringe 11 of the present invention after a single use.

In addition, the adjusting and guiding device 21 has its base of smaller diameter with an interior diameter slightly less than the outside diameter of the hollow piston 17, in order to provide perfect guidance to the piston throughout its stroke, and also to the end that in the as-packed for sale condition the adjusting and guiding device 21 will be the protector of the suction device 18 when placed with light pressure on the end of the hollow piston 17 which carries the suction device 18 (please see FIG. 3).

Another embodiment of the disposable syringe of the present invention is that illustrated in FIG. 5, consisting of a hollow transparent cylindrical body 22 having both its ends open, so that the cartridge containing dental anesthetic 14 presents its end for engaging the needle projecting from the said cylindrical body 22. Accordingly, at the said end there may be included a needle 23 such as those already known in the market to adapt to this type of cartridge of dental anesthetic 14.

The remaining elements of this embodiment are similar to those of the embodiment above first described; that is, curved ears 24 carried on the opposite open end of the cylindrical body 22, a hollow piston 25 which carries at one end curved arms 26 and on the opposite end a suction device (not illustrated) and an adjusting and guiding device 27.

As the consequence of that hereinabove described, we may conclude that the syringe of the present invention affords all of the advantages above indicated, in that some of its elements are applicable in two types of use and in addition it is very practical and economical.

While the foregoing description has been drawn to the specific embodiments of the invention indicated, it will be understood by all those who are expert in the subject matter that any change in form and detail is included within the scope of the present invention.

I claim:

1. A wholly disposable dental type syringe arranged in a packaged-for-sale form and rearrangeable to its disposition for operation, comprising in combination:

a hollow transparent cylindrical body capable of encasing a dental anesthetic cartridge and formed at its interior with ribs extending substantially the entire length of the hollow interior of the cylindrical body to prevent said cartridge from being removed therefrom, which hollow cylindrical body has one end open and the other end closed and is formed integrally with ears at said open end;

an injection needle which has two points at its opposite ends and is mounted in the closed end of said cylindrical body with one of said points projecting into the interior of said cylindrical body so that when the dental anesthetic cartridge is encased in the interior of the cylindrical body, the projecting point is introduced into said cartridge to contact the dental anesthetic;

a hollow piston removably attached to the closed end of the hollow cylindrical body, which hollow piston has one end open and the other end closed and is formed at its open end with curved arms forming an open ring having a clearance between the free ends of the arms substantially equal to the outside diameter of said cylindrical body, the free ends of the curved arms being slightly concave to embrace said cylindrical body;

a harpoon-like device mounted in the closed end of said hollow piston and projecting therefrom; and protecting means removably attached to said hollow piston and covering said harpoon-like device, said protecting means comprising a frustoconical component of annual cross-section, the internal diameter of the smaller end of said component being slightly less than the external diameter of said hollow piston and the external diameter of said smaller end being less than the diameter of the open end of said cylindrical body, the external diameter of the larger end of said component being greater than the external diameter of said open end of the hollow cylindrical body, and the conicity of said frustoconical component being such that said component can be inserted into said open end of the hollow cylindrical body by a distance that is at least equal to the difference between the length of the interior of the hollow cylindrical body and the length of the dental anesthetic cartridge, said frustoconical component and said hollow piston being rearrangeable into said disposition for operation by introducing said frustonical component through the open end of the cylindrical body encasing the dental anesthetic cartridge until said one point of the needle is in contact with the dental anesthetic, and introducing said hollow piston into said cylindrical body through said frustoconical component.

2. The wholly disposable dental type syringe of claim 1, wherein said ribs have a thickness which is greater in their portions registering with said closed end of the hollow cylindrical body and diminishes to a minimum in their portions registering with said open end of the hollow cylindrical body.

* * * * *